US006461870B2

(12) United States Patent
Yatscoff et al.

(10) Patent No.: US 6,461,870 B2
(45) Date of Patent: *Oct. 8, 2002

(54) $^{13}$C GLUCOSE BREATH TEST FOR THE DIAGNOSIS OF DIABETIC INDICATIONS AND MONITORING GLYCEMIC CONTROL

(75) Inventors: Randall W. Yatscoff, Edmonton (CA); Robert T. Foster, Edmonton (CA); Launa J. Aspeslet, Edmonton (CA); Richard Lewanczuk, Edmonton (CA)

(73) Assignee: Isotechnika Inc., Edmonton (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/910,701

(22) Filed: Jul. 20, 2001

(65) Prior Publication Data

US 2002/0042143 A1 Apr. 11, 2002

Related U.S. Application Data

(63) Continuation-in-part of application No. 09/674,806, filed as application No. PCT/IB99/00933 on May 9, 1999.
(60) Provisional application No. 60/084,482, filed on May 6, 1998.

(51) Int. Cl.$^7$ .............................................. G01N 37/00
(52) U.S. Cl. .......................... 436/56; 436/14; 436/173; 436/181; 422/61; 435/14
(58) Field of Search ................................ 436/8, 14, 56, 436/173, 181; 422/61; 435/14

(56) References Cited

U.S. PATENT DOCUMENTS

| | | | | |
|---|---|---|---|---|
| 5,912,178 A | * | 6/1999 | Porter et al. ................... | 436/55 |
| 5,916,538 A | * | 6/1999 | Kohno et al. .................. | 424/9.1 |
| 5,962,335 A | * | 10/1999 | Katzman ....................... | 436/181 |
| 6,067,989 A | * | 5/2000 | Katzman .................... | 422/84 X |
| 6,171,811 B1 | * | 1/2001 | Becerro De Bengoa Vallejo ......................... | 435/34 |

FOREIGN PATENT DOCUMENTS

| | | |
|---|---|---|
| EP | 0826377 A1 | 3/1998 |
| EP | 0913161 A2 | 5/1999 |

OTHER PUBLICATIONS

Röcker et al. *Int. Journal of Sports Medicine*, vol. 17, pp. 480–486, 1996.*
Lifschitz et al. (abstract) *Journal of Pediatric Gastroenterology and Nutrition*, vol. 7(6), pp. 842–847, Nov.–Dec. 1988.*
Beck, Nielsen H., et al., *Metabolic and Genetic Characterization of Pre–diabetic States. Sequence of Events Leading to Non–insulin–dependent Diabetes Mellitus*. J. Clin Invest, 94, (1994), pp. 1714–1721.
Bonora, E., et al., *Homeostasis Model Assessment Closely Mirrors the Glucose Clamp Technique in the Assessment of Insulin Sensitivity*, Diabetes Care, 23, (2000), pp. 57–63.

CDC Diabetes Cost–Effectiveness Study Group, *The Cost –Effectiveness of Screening for Type 2 Diabetes*, JAMA, 280, (1998), pp. 1757–1763.
Emoto, M., et al., *Homeostasis Model Assessment as a Clinical Index of Insulin Resistance in Type 2 Diabetic Patients Treated With Sulfonylureas*, Diabetes Care, 22, (1999), pp. 818–822.
The Expert Committee on the Diagnosis and Classification of DiabetesMellitus, *Report of the Expert Committee on the Diagnosis and Classification of Diabetes Mellitus*, Diabetes Care, 24, (2001), suppl 1.
Gabir, M.M., et al., *The 1997 American Diabetes Association and 1999World Health Organization Criteria for Hyperglycemia in the Diagnosis and Prediction of Diabetes*, Diabetes Care, 23, (2000), pp. 1108–1112.
Ganda, O.P., et al., *Reproducibility and Comparative Analysis of Repeated Intravenous and Oral Glucose Tolerance Tests*, Diabetes, 27, (1978), pp. 715–725.
Haffner, S.M., et al., *A Prospective Analysis of the HOMA Model: The Mexico City Diabetes Study*, Diabetes Care, 19, (1996), pp. 1138–1141.
Harris, M.I., *Undiagnosed NIDDM: Clinical and Public Health Issues*, Diabetes Care, 16, (1993), pp. 642–652.
Helge, A., et al., *Carbon–13 Dioxide Breath Tests in Normal and Diabetic Children Following Ingestion of $^{13}$C–Glucose*, Chemical Abstract Service, Database accession No. 90:37276, XP002120262. (Abstract).
Hirai, A., et al., *The Breath Test Using Pure (1–$^{13}$C) Glucose: A New Simple Method for Evaluating the Glucose Oxidation of Capacity*, Biosciences Information Services, retrieved from STN, XP002120264. (Abstract).
Hosker, J.P., et al., *Continuous Infusion of Glucose with Model Assessment: Measurement of Insulin Resistance and β–cell Function in Man*, Diabetologia, 28, (1985), pp. 401–411.
Ko, G.T.C., et al., *Use of the 1997 American Diabetes Association Diagnostic Criteria for Diabetes in a Hong Kong Chinese Population*, Diabetes Care, 21, (1998), pp. 2094–2097.
Ko, G.T.C., et al., *The Reproducibility and Usefulness of the Oral Glucose Tolerance Test in Screening for Diabetes and Other Cardiovascular Risk Factors*, Ann Clin. Biochem., 35, (1998), pp. 62–67.

(List continued on next page.)

Primary Examiner—Maureen M. Wallenhorst
(74) Attorney, Agent, or Firm—Burns Doane Swecker & Mathis LLP

(57) ABSTRACT

Use of $^{13}$C glucose in an analytical assay to monitor glucose metabolism by measurement of labeled exhaled $CO_2$ is provided. A breath test and kit for performing the breath test are described for the diagnosis of diabetic indications and monitoring of glycemic control. The breath test utilizes the measurement of expired $^{13}$C-labeled $CO_2$ following the ingestion of a $^{13}$C-enriched glucose source.

18 Claims, 8 Drawing Sheets

OTHER PUBLICATIONS

Figure 1:
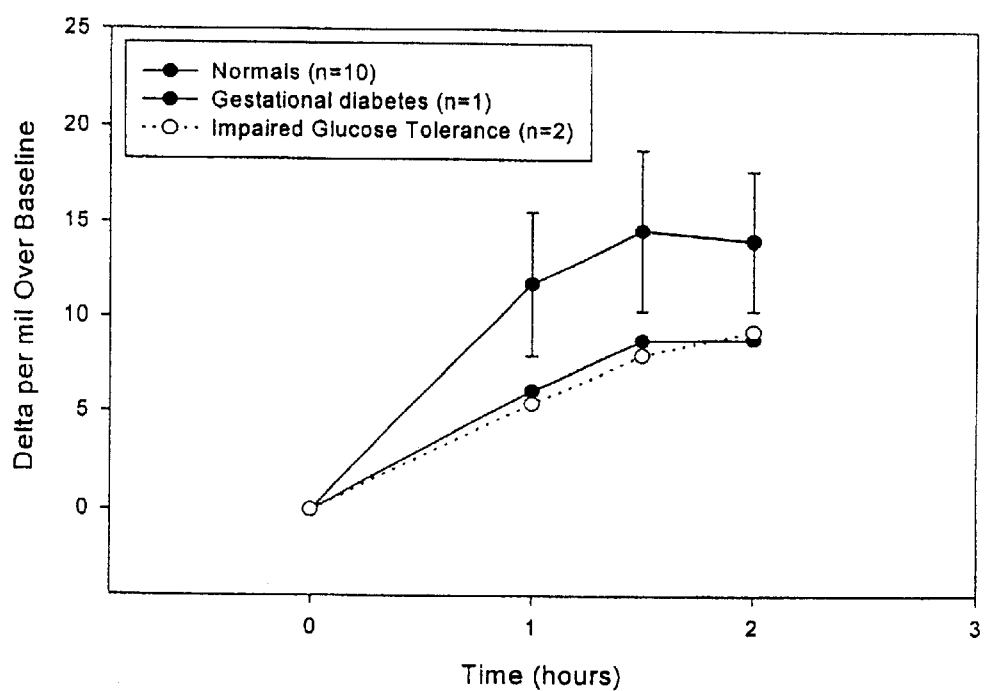

Lillioja, S., et al., *Insulin Resistance and Insulin Secretory Dysfunction as Precursors of Non–insulin–dependent Diabetes Mellitus; Prospective Studies of Pima Indians*, New England Journal of Medicine, 329, (1993), pp. 1988–1992.

Martin, B.C., et al., *Role of Glucose and Insulin Resistance in Development of Type 2 Diabetes Mellitus: Results of a 25–year Follow–up Study*, Lancet, 340, (1992), pp. 925–929.

Matthaei, S., et al., *Pathophysiology and Pharmacological Treatment of Insulin Resistance*, Endocr. Rev., 21, (2000), pp. 585–618.

Matthews, D.R., et al., *Homeostasis Model Assessment: Insulin Resistance and Beta–cell Function from Fasting Plasma Glucose and Insulin Concentrations in Man*, Diabetologia, 28, (1985), pp. 412–419.

McAuley, K., et al., *Diagnosing Insulin Resistance in the General Population*, Diabetes Care, vol. 24, No. 3, (Mar. 2001), pp. 460–464.

Meltzer, S., et al., 1998 *Clinical Practice Guidelines for the Management of Diabetes in Canada.*, Canadian Medical Association Journal, 159, (1998), (suppl. 8): S1–29.

Radziuk, J., *Insulin Sensitivity and Its Measurement: Structural Commonalities Among the Methods*, Journal of Clinical Endocrinol Metab., 85, (2000), pp. 4426–4433.

Riccardi, G., et al., *Reproducibility of the New Diagnostic Criteria for Impaired Glucose Tolerance*, Am. J Epidemiol, 121, (1985), pp. 422–429.

Tanis, A., et al., *Human Liver Glycogen Metabolism Assessed with a $^{13}C$–enriched Diet and a $^{13}CO_2$ Breath Test*, Biosciences Information Services, retrieved from STN, XP002120263. (Abstract).

World Health Organization, *Prevention of Diabetes Mellitus: Report of a WHO Study Group*, Geneva: WHO, (1994), Technical Report Series No. 844.

World Health Organization, *Definition, Diagnosis and Classification of Diabetes Mellitus and its Complications*, Report of a WHO Consultation, Part 1, Diagnosis and Classification of Diabetes Mellitus, Geneva: WHO, (1999).

* cited by examiner

$^{13}$C GLUCOSE BREATH TEST FOR THE DIAGNOSIS OF DIABETIC INDICATIONS AND MONITORING GLYCEMIC CONTROL

REFERENCE TO RELATED APPLICATIONS

This application is a continuation-in-part of U.S. application Ser. No. 09/674,806, filed Feb. 8, 2001, as a U.S. National Phase Application of International Application PCT/IB99/00933, filed May 9, 1999, which claims priority to U.S. Provisional Application No. 60/084,482, filed May 6, 1998. The disclosure of each of the above applications is incorporated herein by reference in their entirety.

FIELD OF INVENTION

Use of $^{13}$C glucose in an analytical assay to monitor glucose metabolism by measurement of labeled exhaled $CO_2$ is provided. A breath test and kit for performing the breath test are described for the diagnosis of diabetic indications and monitoring of glycemic control. The breath test utilizes the measurement of expired $^{13}$C-labeled $CO_2$ following the ingestion of a $^{13}$C-enriched glucose source.

REFERENCES

The following references are referred to by their numbers in parenthesis in this specification.

1. Martin B C, Warram J H, Krolewski A S, et al. Role of glucose and insulin resistance in development of type 2 diabetes mellitus: results of a 25-year follow-up study. Lancet 1992; 340: 925–9.
2. Lillioja S, Mott D M, Spraul M, et al. Insulin resistance and insulin secretory dysfunction as precursors of non-insulin-dependent diabetes mellitus; prospective studies of Pima Indians. N Engl J Med 1993; 329: 1988–92.
3. Beck Nielsen H, Groop L C. Metabolic and genetic characterization of pre-diabetic states. Sequence of events leading to non-insulin-dependent diabetes mellitus. J Clin Invest 1994; 94: 1714–21.
4. Matthaei S, Stumvoll M, Kellerer M, et al. Pathophysiology and pharmacological treatment of insulin resistance. Endocr Rev 2000; 21: 585–618.
5. The Expert Committee on the Diagnosis and Classification of Diabetes Mellitus. Report of the expert committee on the diagnosis and classification of diabetes mellitus. Diabetes Care 2001; 24(suppl 1).
6. Harris M I. Undiagnosed NIDDM: clinical and public health issues. Diabetes Care 1993, 16: 642–52.
7. World Health Organization. Prevention of diabetes mellitus: report of a WHO study group. Geneva: WHO, 1994; technical report series No. 844.
8. Meltzer S, Leiter L, Daneman D, et al. 1998 clinical practice guidelines for the management of diabetes in Canada. Can Med Assoc J 1998; 159 (suppl 8): S1–29.
9. Matthews D R, Hosker J P, Rudenski A S, et al. Homeostasis model assessment: insulin resistance and beta-cell function from fasting plasma glucose and insulin concentrations in man. Diabetologia 1985; 28: 412–19.
10. Haffner S M, Gonzales C, Miettinene H, et al. A prospective analysis of the HOMA model: the Mexico City Diabetes Study. Diabetes Care 1996: 19: 1138–41.
11. Bonora E, Targher G, Alberiche M, et al. Homeostasis model assessment closely mirrors the glucose clamp technique in the assessment of insulin sensitivity. Diabetes Care 2000; 23: 57–63.
12. World Health Organization. Definition, diagnosis and classification of diabetes mellitus and its complications: Report of a WHO Consultation. Part 1. Diagnosis and classification of diabetes mellitus. Geneva: WHO, 1999.
13. Ganda O P, Day J L, Soeldner J S, et al. Reproducibility and comparative analysis of repeated intravenous and oral glucose tolerance tests. Diabetes 1978; 27:715–25.
14. Riccardi G, Vaccaro O, Rivellese A, et al. Reproducibility of the new diagnostic criteria for impaired glucose tolerance. Am J Epidemiol 1985; 121: 422–9.
15. Ko GTC, Chan JCN, Woo J, et al. Use of the 1997 American Diabetes Association Diagnostic criteria for diabetes in a Hong Kong Chinese population. Diabetes Care 1998; 21: 2094–7.
16. Ko GTC, Chan J C N, Woo J, et al. The reproducibility and usefulness of the oral glucose tolerance test in screening for diabetes and other cardiovascular risk factors. Ann Clin Biochem 1998; 35: 62–7.
17. Gabir M M, Hanson R L, Diabelea D, et al. The 1997 American Diabetes Association and 1999 World Health Organization criteria for hyperglycemia in the diagnosis and prediction of diabetes Diabetes Care 2000; 23: 1108–12.
18. Radziuk J. Insulin sensitivity and its measurement: structural commonalities among the methods. J Clin Endocrinol Metab 2000; 85: 4426–33.
19. CDC Diabetes Cost-Effectiveness Study Group. The cost-effectiveness of screening for type 2 diabetes. JAMA 1998; 280: 1757–63.
20. Hosker J P, Matthews D R, Rudneski A S, et al. Continuous infusion of glucose with model assessment: measurement of insulin resistance and β-cell function in man. Diabetologia 1985; 28: 401-11.
21. Emoto M, Kawagishi T, Nishizawa Y, et al. Homeostasis model assessment as a clinical index of insulin resistance in type 2 diabetic patients treated with sulfonylureas. Diabetes Care 1999; 22:818-22.

The entire disclosure of each of the above-referenced publications, patents and patent applications is incorporated herein in its entirety.

BACKGROUND OF THE INVENTION

Glucose tolerance is defined as the ability to properly utilize glucose. Diabetes is not a single disease, but an array of diseases that exhibit the common symptom of glucose intolerance, an impairment in glucose utilization.

The prevalence of diabetes in the general population is approximately 6-7%. Only about half of diabetics are actually diagnosed. Studies have shown that rates for persons with glucose intolerance are equal by sex and greater for blacks than for whites.

In general, the following types of diabetes have been recognized: type I diabetes mellitus, type II diabetes mellitus, secondary diabetes mellitus, impaired glucose tolerance and gestational glucose mellitus. The general characteristics of the symptoms of diabetes include the following:

Polyuria (excretion of large quantities of urine)
Hyperglycemia (high blood glucose levels)
Glucosuria (abnormal presence of glucose in urine)
Polydipsia (excessive thirst)
Polyphagia (excessive hunger)

Sudden weight loss

It has been observed that complications resulting from diabetes mellitus are the third leading cause of death in most developed countries. Diabetes is a risk factor for a variety of conditions including coronary heart disease, cerebrovascular stroke, neuropathy (nerve damage), nephropathy (kidney damage), retinopathy (eye damage), hyperlipidemia (excessive blood lipids), angiopathy (damage to blood vessels) and infection.

A number of different methods exist for determining a condition of intolerance for glucose. These include postprandial blood glucose, oral glucose tolerance test (OGTT), O'Sullivan glucose tolerance test (gestational test), hemoglobin Alc (Hb $A^1$, Hb $A_{1c}$), islet cell antibodies, glutamic acid decarboxylase (GAD) antibodies and insulin antibodies. Diabetes, however, is most readily detected when the carbohydrate metabolic capacity is tested. This is done by stressing the system with a defined glucose load as in the oral glucose tolerance test (OGTT).

The OGTT has been criticized, however, because many of the variables affecting test results are difficult to control. For instance: patients must be on a standardized carbohydrate diet at least three days before the test; the test requires an 8 to 16 hour fast; the test should only be performed on ambulatory patients; stress should be avoided; exercise should be avoided; various hormone imbalances can affect validity such as with: thyroxine, growth hormone, cortisol and catecholamines; various drugs and medications can affect validity such as: oral contraceptives, salicylates, nicotinic acid, diuretics and hypoglycemics; and evaluation should normally be corrected for age. The greatest disadvantage of the OGTT is that it is poorly reproducible and this limits its diagnostic usefulness.

Type 2 diabetes is a common condition, associated with significant morbidity and mortality. It is generally acknowledged that overt type 2 diabetes is preceded by a period of glucose intolerance which itself is preceded by a significant period of insulin resistance (1–5). It is now further recognized that typical diabetic complications can begin to develop during this "pre-diabetic" phase (3, 6). The identification of persons at risk of developing overt type 2 diabetes has therefore taken on even greater importance. It has been suggested that if such persons could be easily identified, a lifestyle modification strategy could be implemented which might prevent their progression to type 2 diabetes with its attendant morbidities.

Because of the public health importance of type 2 diabetes, regular screening for this condition is now advocated (5, 7, 8). However, such screening programs, whether by fasting plasma glucose or by the 75-g OGTT, only identify diabetic or glucose-intolerant patients. The homeostasis model assessment (HOMA) index has been advocated as a method of detecting persons with insulin resistance and therefore presumably at risk of progressing to overt type 2 diabetes (9–11). However, the HOMA index requires a serum insulin measurement and, some argue, the use of a computer program. Thus, this index is not as simple or accessible as a fasting blood glucose level. Similarly, the gold standard euglycemic, hyperinsulinemic clamp is clearly not appropriate for mass screening campaigns.

The current methods of diagnosing diabetes involve either invasive testing (i.e., repeated blood collections), or use blood-borne markers (i.e., glycosylated proteins, or antibodies) which offer an indirect assessment of glucose regulation. Accordingly, it is an object of the present invention to avoid the need for invasive testing or the use of blood-borne markers in determinations of glucose regulation.

SUMMARY OF THE INVENTION

The above and other objects of the invention are attained by a $^{13}C$ breath test and a kit for determining glucose regulation in a patient in need thereof.

Based on our experience in the use of $^{13}C$ breath tests, we propose a simple, sensitive test of insulin resistance. In normal individuals, in the presence of insulin, glucose is taken up by cells where it undergoes glycolysis and then enters the citric acid cycle or is shunted to fat synthesis. In either case, $CO_2$ is produced as a metabolic by-product. This $CO_2$ then re-enters the circulation and is eliminated in the lungs. We found that if glucose was labeled with $^{13}C$, the resultant $CO_2$ could be detected in the expired air. In type 2 diabetes and other states of insulin resistance, glucose uptake is impaired and the generation of $^{13}CO_2$ is likewise blunted. Accordingly, we have developed a $^{13}C$-glucose breath test for the diagnosis of type 2 diabetes and insulin resistance. In particular, the test provides a means to detect insulin resistance when blood glucose levels are still in the normal range and before β-cell destruction leading to diabetes has occurred. Early detection of insulin resistance will allow intervention in time to prevent the development of type 2 diabetes. In addition, the test allows the success of intervention therapies, including diet and exercise. to be monitored.

An analytical assay is described that is based on the use of non-radioactive $^{13}C$. Labeled expired $^{13}CO_2$ is measured in the present assay. Isotope ratio mass spectroscopy (IRMS) is used as a detection method for $^{13}C$, a non-radioactive isotope that occurs naturally in food and animal tissues. Non-dispersive infrared spectroscopy (NDIRS) analysis and analysis methods known in the art may be employed. The test protocol is as follows: after an overnight fast, the oral dose of $^{13}C$ uniformly labeled glucose (containing about 25 mg of $^{13}C$ glucose in combination with about 15 g of unlabeled glucose in 100 ml of tap water) is administered. Breath samples will be collected before the dose and then 1½ hours after $^{13}C$ glucose ingestion. Levels of $^{13}CO_2$ in expired air will be measured by an IRMS method.

Advantages of this test are the following:
it is practical, sensitive and specific;
the validity of the test is not influenced by stress, exercise, hormone imbalances, or some drugs and medications;
it is a non-invasive method;
it is simple to perform and can be readily used in physicians' offices or medical laboratories;
it is safe since $^{13}C$ is a naturally occurring isotope found in all carbon-containing substances;
it involves no radioactivity, and may be used in children and women.

The $^{13}C$ glucose test is safe, reliable, and specific in diagnosis of diabetes and measurement of the severity of insulin resistance in patients. The invention is also preferred to diagnose gestational diabetes and to monitor glycemic control in diabetes patients. A preferred embodiment of the invention is a kit containing the necessary material for performing the described method. This kit may contain, but is not limited to, a source of $^{13}C$ enriched glucose (preferably uniformly labeled D-glucose); a source of unenriched glucose; and a breath collection device. The kit may also contain a set of patient instructions for its use. In another embodiment, the kit may additionally contain a blood collection device, such as a lancet or hypodermic needle and vacutainer for the additional determination of blood glucose levels.

Accordingly, in one aspect the invention provides diagnostic kits for the determination of glycemic control in a subject comprising: a predetermined quantity of $^{13}C$-enriched glucose; and a breath collection container. A plurality of breath containers and/or instructions for use may be included. The kits may be used for the diagnosis of diabetes, insulin resistance, gestational diabetes, and the like or to determine the adequacy of antihyperglycemic therapy.

In a further aspect, the invention provides a use of $^{13}C$-enriched glucose for the determination of glycemic control in a subject.

In another aspect, the invention provides $^{13}C$-enriched glucose for use in the manufacture of diagnostic kits for the determination of glycemic control in a subject. The kits may be used for the diagnosis of diabetes, insulin resistance, gestational diabetes, and the like or to determine the adequacy of antihyperglycemic therapy.

In yet a further aspect, the invention provides diagnostic kits for the determination of glycemic control in normal, diabetic and insulin resistant subjects by comparing blood glucose levels with breath levels of $^{13}C$-enriched $CO_2$ In a still further aspect, the invention provides method of diagnosing a condition in a subject, said condition selected from the group consisting of diabetes, insulin resistance impaired glucose tolerance, impaired fasting glucose and gestational diabetes, said method comprising collecting a first breath sample from said subject in a first breath collection container; administering $^{13}C$-enriched glucose to said subject; collecting a second breath sample from said subject in a second breath container at a time point after administration of said $^{13}C$-enriched glucose; measuring the $^{13}CO_2$ in each of said first and second breath samples; and comparing the amount of $^{13}CO_2$ in said second breath sample with the amount of $^{13}CO_2$ in said first breath sample to obtain a delta value, wherein the presence of less $^{13}CO_2$ in said second breath sample compared to normal control values indicates the presence of said condition. Using an ROC curve, a delta cutoff is chosen wherein the sensitivity and specificity are such as to maximize diagnostic accuracy. In particular, when the condition is insulin resistance, a range of deltas from 8 to 10 is preferred. A delta of 9 is most preferred.

In yet an additional aspect, the invention provides method of predicting a subject's risk of developing diabetes, said method comprising collecting a first breath sample from said subject in a first breath collection container; administering $^3C$-enriched glucose to said subject; collecting a second breath sample from said subject in a second breath container at a time point after administration of said $^{13}C$-enriched glucose; measuring the $^{13}CO_2$ in each of said first and second breath samples; and comparing the amount of $^{13}CO_2$ in said second breath sample with the amount of $^{13}CO_2$ in said first breath sample, wherein the presence of less $^{13}CO_2$ in said second breath sample compared to normal control values indicates risk of developing diabetes. The comparison may be made by choosing a cutoff of ROC values wherein the sensitivity and specificity are such as to maximize diagnostic accuracy. In particular, a range of ROC's from 8 to 10 is preferred. An ROC of 9 is most preferred.

The $^{13}C$-glucose breath test is superior to currently used laboratory criteria in the diagnosis of type 2 diabetes. Its predictive value for clinical status, as well as its correlation with the HOMA index, make it a simple but useful test for detecting early evidence of insulin resistance and hence, risk for type 2 diabetes.

BRIED DESCRIPTION OF THE DRAWING FIGURES

FIG. 1: Illustrates the IRMS analysis of $^{13}C$ glucose breath samples from normal individuals, a gestational diabetic, and patients with impaired glucose tolerance.

Figure 2:
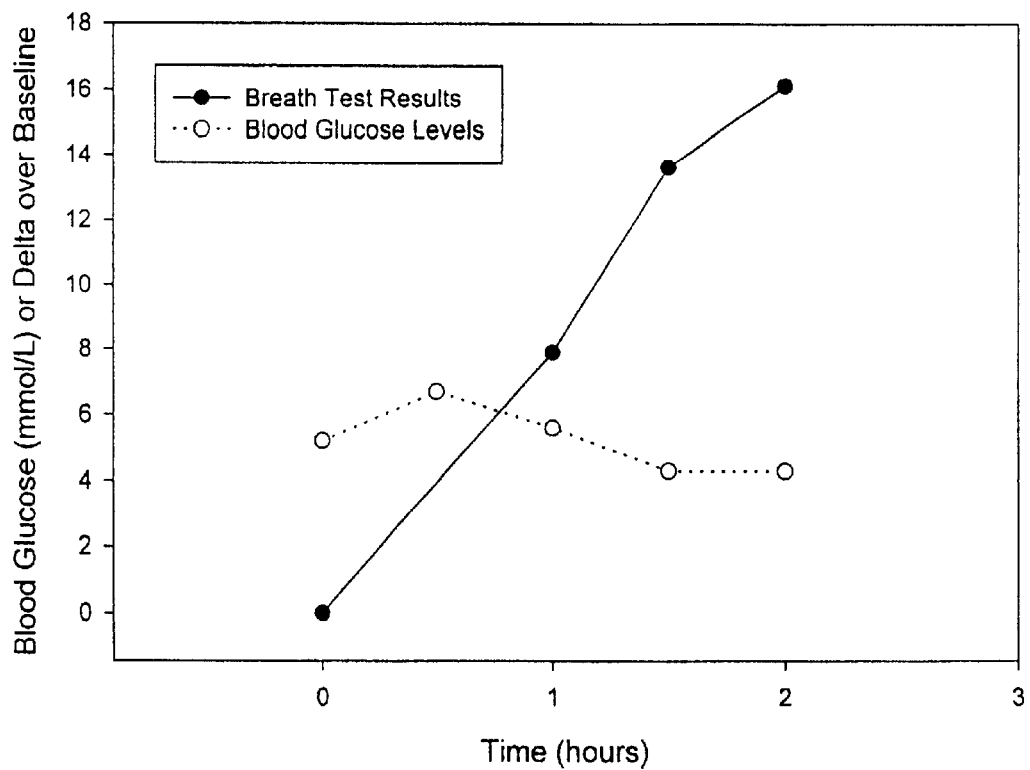

FIG. 2: Shows a representative example of breath test and blood glucose levels of a normal individual.

Figure 3:
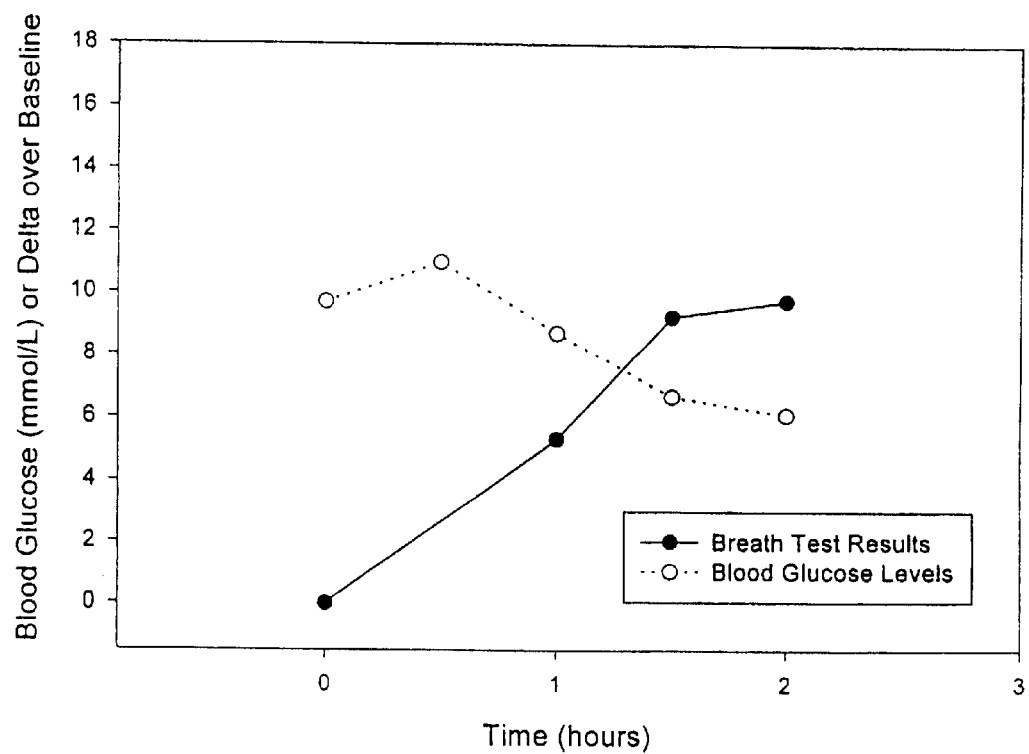

FIG. 3: Illustrates breath test and blood glucose levels of a diabetic patient.

Figure 4:
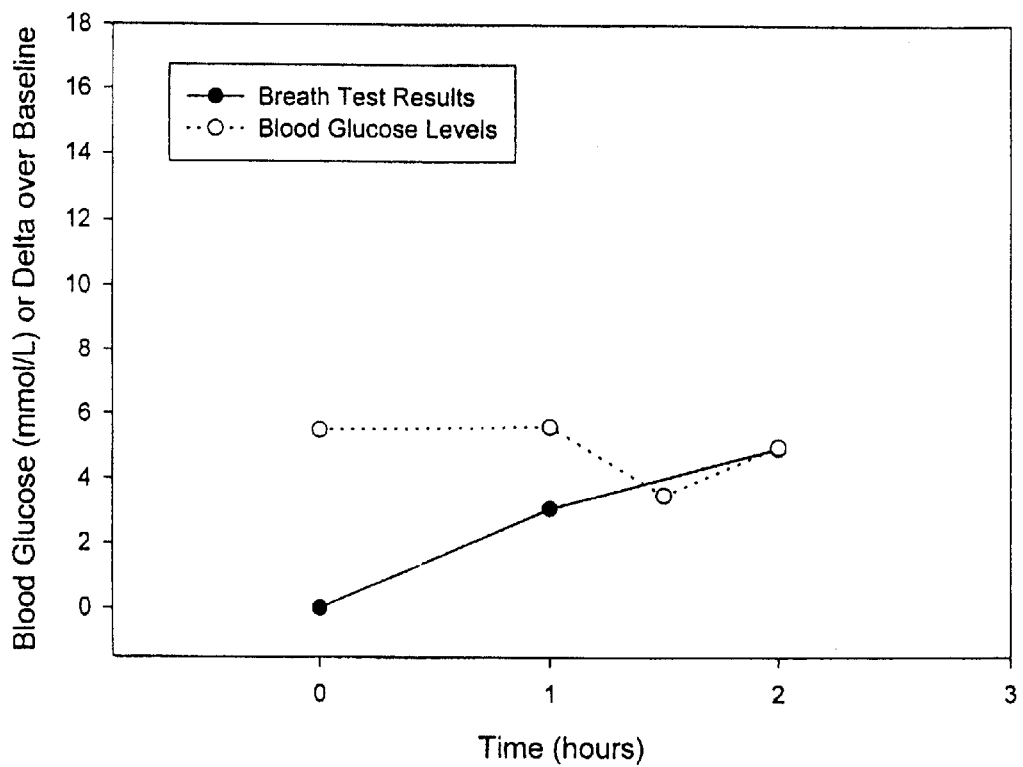

FIG. 4: Depicts breath test and blood glucose levels of an insulin resistant patient.

Figure 5:
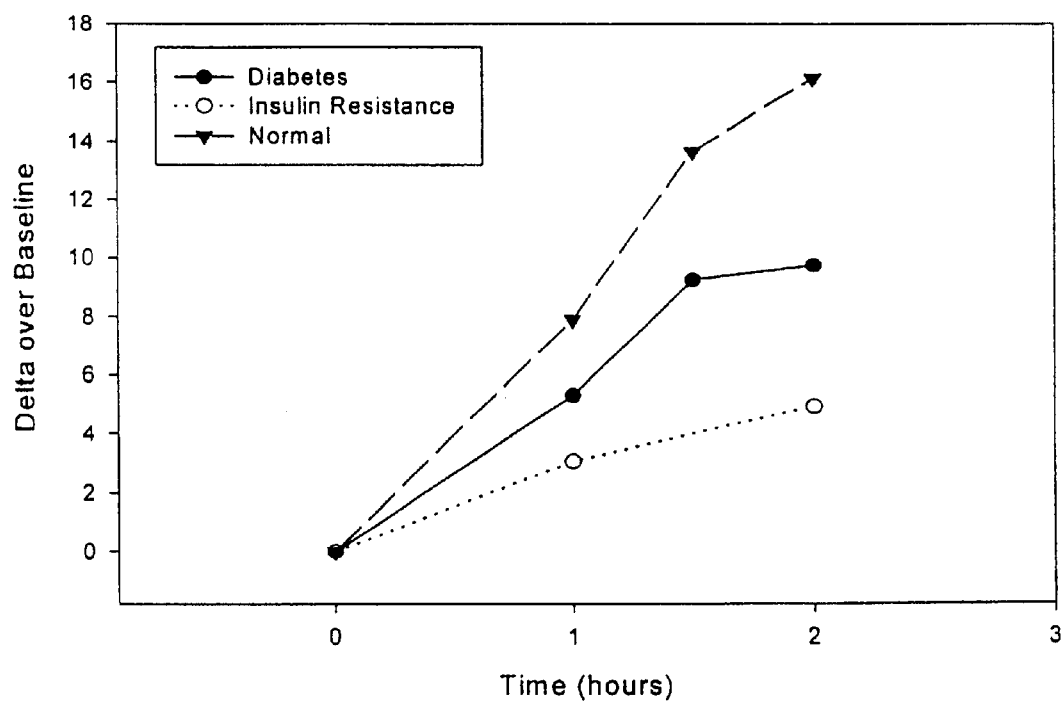

FIG. 5: Shows a comparison of IRMS results of an insulin resistant and a diabetic patient, and a normal individual.

FIG. 6: Illustrates the distribution of $^{13}CO_2$ (a) and HOMA (b) results between diabetic and non-diabetic patients. Bars indicate the upper limit of the normal range.

Figure 7:
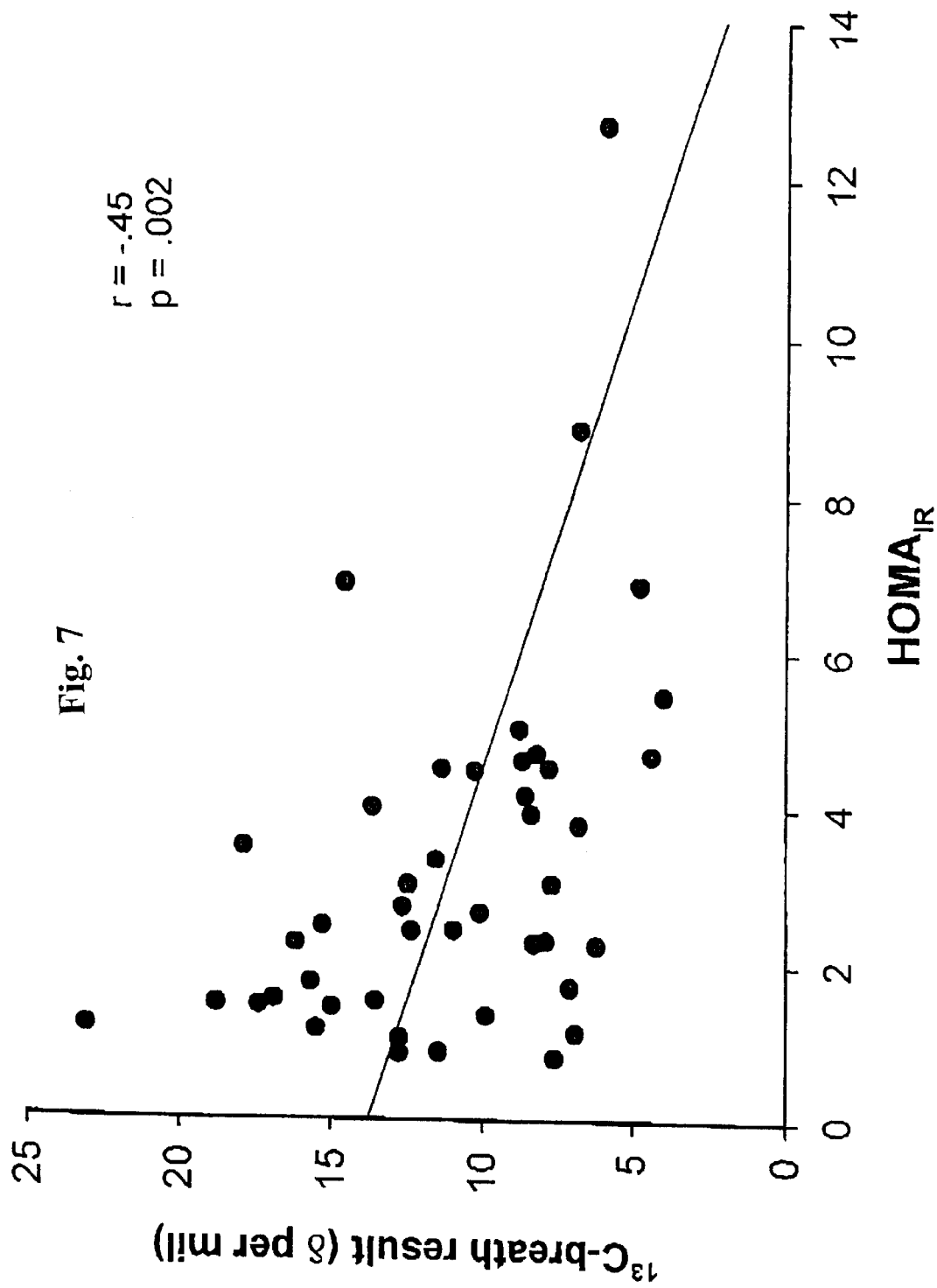

FIG. 7: Plots the relationship between HOMA index and $^{13}C$-glucose breath test result.

Figure 8:
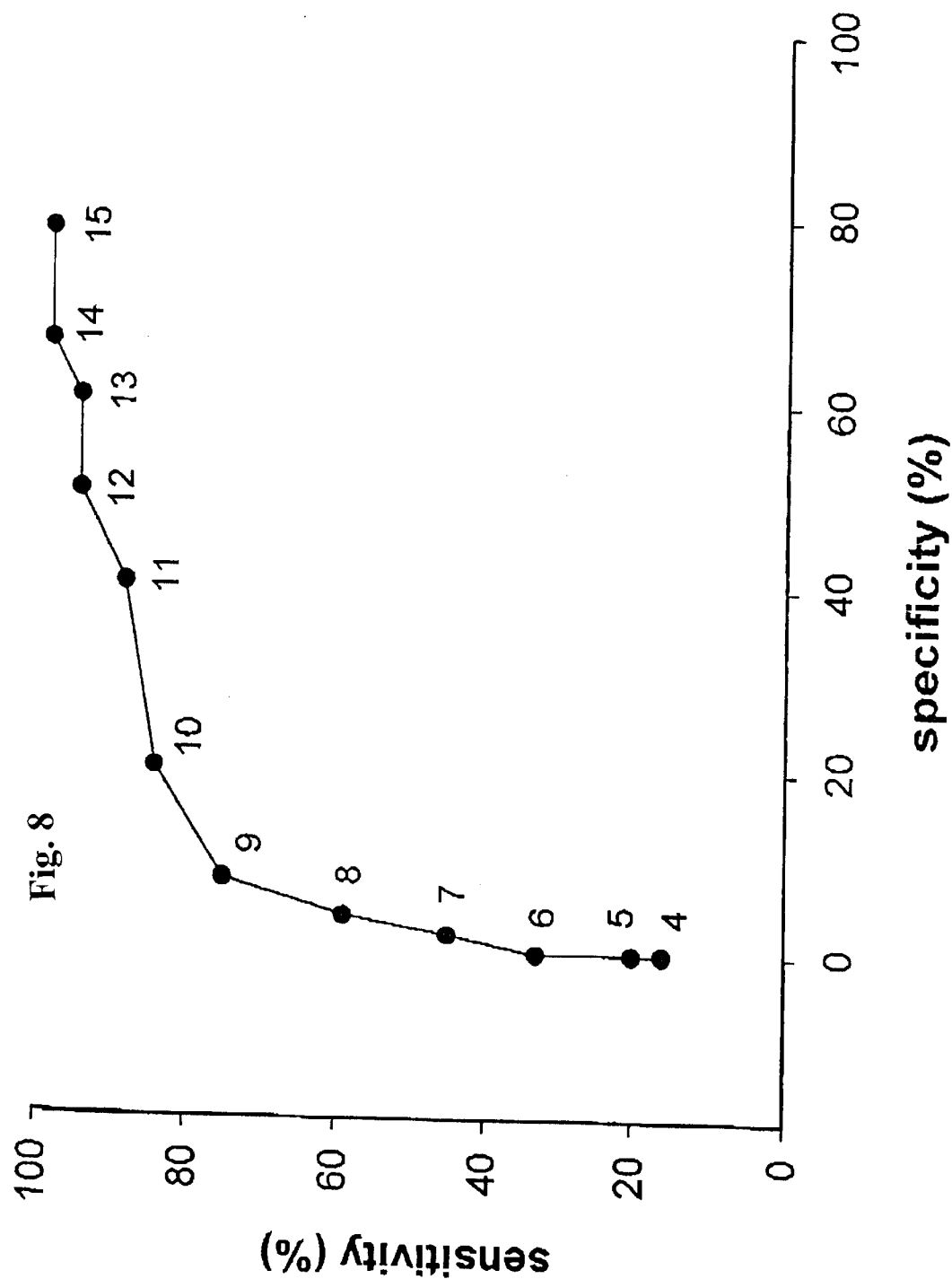

FIG. 8: Illustrates the ROC curve for the $^{13}C$-glucose breath test. Individual points are in δ per mil.

DETAILED DESCRIPTION OF THE INVENTION

The introduction of a $^{13}C$ breath test offers a novel, non-invasive, direct means to monitor glucose metabolism by measurement of exhaled $CO_2$ using highly enriched, uniformly labeled $^{13}C$-glucose. Glucose metabolism will generate labeled $CO_2$, which is then exhaled and collected in tubes. Enrichment of labeled $CO_2$, over a determined time course, can be used as a quantitative index of glucose metabolism. Comparison is made against age-specific reference intervals.

The present invention has a number of advantages, including lower dose of glucose needed (overcomes inconsistencies due to malabsorptive disorders or previous gastric or intestinal surgery), reduction in testing time (from the current 2 hours required for the OGTT) and fewer interpretational ambiguities (greater sensitivity and specificity).

The $^{13}C$ glucose breath test is based on the metabolism of glucose. Following a baseline breath sample, a $^{13}C$ glucose solution containing about 25 mg of $^{13}C$ glucose in combination with about 15 g of unlabeled glucose in 100 ml of tap water is administered. Breath samples will be obtained before the dose and then 12 hours after $^{13}C$ glucose ingestion. Measurement of the expired air will be detected by an isotope ratio mass spectroscopy assay method. Elevated or excessive breath of $^{13}CO_2$ concentrations will be seen in individuals who have normal glucose metabolism.

The $^{13}C$-glucose breath test provides a more sensitive and diagnostically accurate indicator of the presence of type 2 diabetes than do currently used common methodologies. However, a problem arises in that the definition of diabetes is made on the basis of fasting plasma glucose or glucose-tolerance test values. Thus, these tests are the de facto "gold standards" and theoretically should be the most accurate. In the well-characterized group of diabetic patients studied in this investigation, the pitfalls of a single fasting blood glucose value or a glucose tolerance test are evident. Indeed, numerous reports of the poor overall diagnostic accuracy of the glucose tolerance test or fasting plasma glucose as a diagnostic tool for diabetes exist (13–17). Moreover, the requirement for confirmation of an abnormal fasting plasma glucose reduces sensitivity of this test albeit at a gain in specificity. It could be argued, however, that for screening purposes, sensitivity is perhaps preferable to specificity. However, because of the theoretical advantage of diagnosing subjects at risk of diabetes prior to the actual onset of the disease, various indices of insulin resistance or glucose intolerance have been devised (for a review see 18). The hypothesis associated with these latter measurements is that insulin resistance and abnormalities in glucose homeostasis occur well before the onset of overt type 2 diabetes. If patients demonstrating such abnormalities can be detected through screening programs, it has been suggested that the development of overt diabetes may be prevented or delayed (4, 5, 19). The importance of such an approach is further underscored by the finding that at the time of type 2 diabetes onset, a significant number of patients already have diabetic complications (3, 6).

In order to address the need for a relatively simple index of insulin resistance, the HOMA index was developed. This index has been shown to correlate with results from the gold-standard hyperinsulinemic, euglycemic clamp (9, 11, 20, 21). Although the HOMA index was significantly higher in the diabetics in this study, it was diagnostically inferior in all aspects to the $^{13}$C-glucose breath test. Indeed, when both the HOMA index and the $^{13}$C-glucose breath test results were entered into a logistic regression which included fasting blood sugar, age, sex and BMI as variables, only the $^{13}$C-glucose breath test gave a statistically significant partial correlation coefficient. Similarly, when each of the two variables of interest was individually included in a similar logistic regression, which also included the 2 hour OGTT value as a further variable, the $^{13}$C-glucose breath test retained a statistically significant predictive value whereas the HOMA index did not. Indeed, in all possible iterations of the logistic regression, the $^{13}$C-glucose breath test was always the strongest predictor of diabetic status. Although it may be argued that a HOMA is an easier test, requiring only a single blood sample, there are disadvantages to this test as well. First of all, a serum insulin measurement must be carried out in a reasonably advanced medical laboratory by trained technicians. This adds time and cost to the screen. The $^{13}$C-glucose breath test, however, can be analyzed using a point of care instrument that requires very little training to use. Thus, screening can be carried out in the field with results available almost as soon as the last breath sample is complete. The HOMA index requires blood samples with the attendant infectious precautions. The $^{13}$C-glucose breath test is carried out on breath and therefore only general infectious precautions are necessary. Similarly, phlebotomy requires trained medical personnel whereas the $^{13}$C-glucose breath test does not necessarily require any supervision—a package insert can provide all the necessary instructions. Thus, the $^{13}$C-glucose breath test can also be made available to remote locations via post. Finally, although the HOMA provides added diagnostic accuracy to the diagnosis of diabetes when compared to a fasting blood sugar, as can be seen from Table 1, the traditional OGTT is superior to both. Compared to the OGTT, however, the $^{13}$C-glucose breath test has even greater accuracy and has the advantage of requiring a lower glucose load and a shorter time requirement along with all the other advantages listed above. One final consideration is the possibility of false negative results with the breath test in subjects with delayed gastric emptying. Given the relatively low volume and lower osmolarity of the breath test compared with the OGTT, problems with gastric emptying are likely to be less than those associated with the OGTT. Indeed, based on 1, 1.5 and 2 hour breath test values in this study, no subjects showed evidence of delayed gastric emptying. As this test is most likely to find use early in the course of insulin resistance/type 2 diabetes, it is unlikely that diabetic gastroparesis will be a significant confounder. Thus, the $^{13}$C-glucose breath test offers a simple, sensitive and accurate method for the diagnosis of type 2 diabetes.

In terms of insulin resistance, studies are underway to validate the $^{13}$C-glucose breath test against the hyperinsulinemic, euglycemic clamp. However, even with the current results, there is evidence that the $^{13}$C-glucose breath test is an indicator of insulin resistance. First, the $^{13}$C-glucose breath test results do correlate with the HOMA. Secondly, there is a strong correlation between the breath test and body mass index whereas the correlation between the HOMA index is less strong. Third, the superior diagnostic parameters of the breath test and the fact that a type 1 diabetic had a breath result of <1.2 show a correlation between insulin resistance and the $^{13}$C-glucose breath test result. Finally, the underlying principal of the $^{13}$C-glucose breath test is based on resistance to glucose uptake by target tissues. Thus, the $^{13}$C-glucose breath test also offers a simple, sensitive, specific test for the diagnosis of insulin resistance.

One final advantage of the $^{13}$C-glucose breath test is its application for following insulin resistance. This test has the potential to allow the effectiveness of various interventions in type 2 diabetes to be monitored. Whether these interventions be lifestyle or pharmacological, the $^{13}$C-glucose breath test offers a sensitive, dynamic method to assess effectiveness of type 2 diabetes treatments.

Thus, the $^{13}$C-glucose breath test may be used not only to diagnose diabetes, but also to determine insulin sensitivity and insulin resistance. The test may reliably be used to diagnose other difficult to detect pre-diabetic conditions. Thus, it is a useful tool to determine whether a patient is at risk of developing diabetes.

It is important that any diagnostic test procedure have diagnostic accuracy, i.e., that it accurately predicts positive and negative values. The receiver operated characteristics (ROC) value describes the balance between the sensitivity (i.e., the number of hits detected) and the specificity (i.e., the accuracy) of a test. These two variables may also be considered positive predictive value and negative predictive value, and are correlated with diagnostic accuracy. The ROC curve shows the relationship of the probability of a positive test, given no disease, to the probability of a positive test, given disease. An ROC cutoff value is chosen to maximize diagnostic accuracy of the test in question.

The following examples serve to illustrate the present invention. These examples are not intended to limit the scope of the invention in any manner.

EXAMPLE 1

Sample Assay for Diagnosis of a Patient

Experimental Procedure

Medical History

Medical history is taken and includes, but is not limited to: the absence of active pulmonary disease, no history of heart, liver, or renal failure, and no use of insulin or oral medications for the treatment of diabetes.

Physical Examination and Laboratory Tests

No physical examination or laboratory tests, including blood sampling, is required.

Dietary Control

It is determined that all participants have fasted overnight prior to commencement of the test.

Patient Control

Participants are not permitted to eat, drink, or smoke during the test. All patients are required to remain sedentary for the duration of the test. Small amounts of water are allowed.

Assay Procedure

Patients fast for at least 8 hours before this test.

A sample set of patient instructions is given below:

Step 1: COLLECT FIRST BREATH SAMPLE

Remove the screw cap from the collection tube.

Take a normal breath and then exhale fully 4 to 8 seconds through a straw into the bottom of the collection tube.

Immediately replace the screw cap on the collection tube and tighten until snug (do not overtighten).

Affix the completed green label to the collection tube.

Step 2: DRINK THE SOLUTION

Prepare the solution by adding tap water to the fill line on the plastic container. Mix until completely dissolved and then drink the entire solution.

Wait 1½ hours.

Step 3: COLLECT THE SECOND BREATH SAMPLE

One and one half hours after drinking the solution, collect the second breath sample into the collection tube following the same directions as for the first breath sample in step 1.

Affix the completed yellow label to the tube.

Step 4: RETURN THE SAMPLES FOR ANALYSIS

Insert the 2 collection tubes along with the signed and completed registration card in the mailing box.

Return the mailing box as instructed to the site of dispensing.

EXAMPLE 2

Breath Test Administration

Patients are given an exetainer tube with the screw cap removed. Using the straw, they are asked to breathe into the tube, exhaling normally, for 4 to 8 seconds. Next, each patient is instructed to drink a solution containing about 25 mg of uniformly labeled $^{13}C$ glucose in combination with about 15 g of unlabeled glucose in 100 ml of tap water. After 12 hours, the patients are given a new tube to breathe in as described above. The breath collection is then complete.

Storage and Shipping

Breath test tubes are typically labeled with the patient's name and identification number and shipped to an analytical laboratory for analysis. No refrigeration or special storage techniques are necessary.

EXAMPLE 3

Analytical Methodology

Breath specimens are analyzed by isotope ratio mass spectroscopy. NDIRS is also a preferred method to analyze breath test samples. Other methods known in the art may also be used.

Statistical Analysis

The sensitivity, specificity, positive and negative predictive values of the breath test are compared to that of the oral glucose tolerance test. Receiver operated characteristic curve (ROC) analysis is performed to confirm the discrimination between type 2 diabetes or gestational diabetes and individuals with normal glucose metabolism.

EXAMPLE 4

Basis of the Method of IRMS

Isotope ratio mass spectroscopy (IRMS) is a highly precise method of analysis which is able to measure small samples (low nanogram amounts). For example, $^{13}C/^{12}C$ ratios are determined on a mono-carbon molecule; $CO_2$ gas. The $CO_2$ gas can be directed to the spectrometer by means of a continuous flow IRMS (also called CF-IRMS).

The statistical combination of the isotopes of carbon ($^{12}C$ and $^{13}C$) and oxygen ($^{16}O$, $^{17}O$, $^{18}O$) to generate the $CO_2$ molecules gives rise to the formation of various isotopomers whose molecular weights are 44, 45, and 46, respectively. Thus, for measuring carbon isotope ratios, 3 ion beams are generated and recorded in the IRMS, corresponding to the masses of the various isotopomers of $CO_2$.

In order to obtain a high precision and a high accuracy, reference gases of absolutely known isotopic composition are used and a dual inlet system allows an alternative admission of both sample and reference gases into the ionization source via a gas-switching valve. The measurement of the various ion beams allows for the calculation of the $^{13}C$ enrichment of the sample. The value of this calculation is given $\delta^{13}C(‰)$ notation. The $^{13}C$ abundance is expressed as $\delta^{13}C(‰)$ according to the following:

$$\delta^{13}C(‰) = ([^{13}C/^{12}C)\text{sample}/(^{13}C/^{12}C)\text{PDB}]-1) \times 1000$$

This $\delta^{13}C(‰)$ value measures the variations in parts per thousand of the carbon isotope ratio from the standard. For carbon, PDB was selected as the international reference. PDB is Pee Dee Belemnitella (a fossil from the Pee Dee geological formation in South Carolina). The $^{13}C/^{12}C$ ratio from the calcium carbonate of this fossil is 0.011237. Compared to PDB, most of the natural compounds display a negative delta value. In the above equation, $^{13}C/^{12}C$ refers to the isotopomers.

Using the breath test of this invention, IRMS is an example method to diagnose type 2 and gestational diabetes, and for monitoring glycemic control of diabetes patients.

EXAMPLE 5

$^{13}C$ Glucose Breath Test Results of Normal, Gestational Diabetes and Impaired Glucose Tolerance Patient Example 4 describes a method to analyze breath samples of this invention. FIG. 1 shows the mean (±SD) Delta per mil over Baseline (DOB) of the normal population. Also shown are the DOB's of a gestational diabetic and impaired glucose tolerance patients. Breath samples collected 0, 1, 1.5 and 2 hours according to the protocol were analyzed by IRMS. IRMS analysis of the collected breath samples can be performed on various instruments including, but not limited to, the AP2003 and AP2002 (Analytical Precision Ltd.), ABCA (POZ Europa) and the Breath MAT (Finnigan MAT). The DOB values of the gestational diabetes and the impaired glucose tolerance patients are well below the DOB of the normal population (FIG. 1). The impaired glucose tolerance diagnosis was initially determined by OGTT, the gestational diabetes screen was used to confirm gestational diabetes.

Impaired glucose tolerance (IGT) refers to a condition in which blood sugar levels are higher than normal, but are not high enough to be classified as diabetes. IGT is a major risk factor for type 2 diabetes. IGT is present in about 11 percent of adults, or approximately 20 million Americans. About 40–45 percent of persons age 65 years of age or older have either type 2 diabetes or IGT. A person is currently diagnosed with IGT when the 2-hour glucose results from a glucose tolerance test are greater than 7.8 mmol/L, but less than 11.0 mmol/L. A woman is diagnosed with gestational diabetes when she is pregnant and has any two of the following: a fasting plasma glucose of more than 5.3 mmol/L, a 1-hour glucose level of more than 10.6 mmol/L, a 2-hour glucose level of more than 8.9 mmol/L. However, as this method of diagnosis is invasive, the breath tests of the current invention is the preferred diagnosis method. The $^{13}C$ glucose breath test is sensitive, accurate and non-invasive.

EXAMPLE 6
$^{13}$C Glucose Breath Test Results of a Normal, Insulin Resistant and Diabetes Patient In this example, both breath test and blood glucose levels were done on a normal, diabetic and insulin resistant patient. FIG. 2 shows the DOB of 0, 1, 1.5 and 2 hours breath samples of a normal subject analyzed by IRMS. The blood glucose level of this normal individual is also displayed.

FIG. 3 illustrates the breath test and blood glucose levels of a diabetic patient. The DOB of the breath samples are significantly lower than the DOB of the normal individual (FIG. 2), the blood glucose levels are typical of a diabetic patient.

In FIG. 4, the breath test and blood glucose levels of an insulin-resistant patient are depicted. The DOB of these breath samples are significantly lower than the normal DOB (FIG. 2), the blood glucose levels are typical of an insulin-resistant patient.

These results demonstrate one preferred utility of the breath test of the current invention to diagnose diabetes and insulin resistance. In another aspect of the invention, the areas between the breath test and blood glucose test curves can be used to diagnose patients with insulin resistance or diabetes and confirm glucose tolerance in normal individuals by the comparison of the areas to the different groups of normal, diabetic and insulin resistant patients.

FIG. 5 illustrates the $^{13}$C glucose breath test results of a normal individual, insulin resistant and diabetes patient. The DOB's of the insulin resistant and diabetes patients is significantly lower than that of the normal DOB results.

EXAMPLE 7
NDIRS Instrumentation

Breath test samples of the invention can also be analyzed using NDIRS instrumentation. The course of the $^{13}CO_2/^{12}CO_2$ ratio in breath allows for diagnosis of diabetes. NDIRS can be further used to diagnose type 2 and gestational diabetes patients and for monitoring therapy of diabetes patients (glycemic control of these patients).

The metabolism of $^{13}$C labeled substrate leads to a different isotope ratio. NDIRS analysis of the invention can be performed on various instruments, including, but not limited to, the MicroLyzer (QuinTron), UbiT-IR200 andUbiT-100 (Otsuka Pharmaceutical Co., Ltd.), the URAS 10 (Hartmann and Braun) and the Isomax 2000 (Isotechnika).

EXAMPLE 8
Hyperinsulinemic Euglycemic Clamp Method for the Measurement of Insulin Resistance Insulin resistance is defined as the decrease of the biological action of insulin, and it mainly presents as an hyperinsulinemia. The hyperinsulinemic euglycemic clamp is currently the reference method for quantifying insulin resistance. The clamp technique consists of infusing insulin at a constant rate and, to prevent any decrease in the plasma glucose level, by infusing dextrose. The rate of dextrose infused to maintain euglycemia is an estimate of the amount of glucose, which is taken up by the tissues under the effect of a defined plasma insulin concentration. Using several rates of insulin infusion allows the establishment of the relationship between the whole body glucose disposal and plasma insulin levels, and to discriminate between the states of decreased insulin sensitivity and/or altered maximal capacity to dispose of glucose. However, the hyperinsulinemic euglycemic clamp method is very invasive, time consuming, costly and variable. The breath test of this invention is a preferred method to measure insulin resistance as it is reliable, sensitive, specific, cost-effective and non-invasive.

EXAMPLE 9
Monitoring Long-term Control of Diabetes

Measuring glycated hemoglobin is a current test used for monitoring long-term control of diabetes. Glycated hemoglobins are increased as a reflection of hyperglycemia during the life span of erythrocytes. However, different analytical methods may measure different glycated hemoglobins and caution must be exercised in the interpretation of results. HPLC or column chromatography methods used to analyze glycated hemoglobin are also highly sensitive to variations in temperature and pH. This test is also invasive, requiring several blood samples. The breath test of the present invention is preferred as it is non-invasive, sensitive, accurate and cost-effective.

EXAMPLE 10
Usefulness of $^{13}$C Glucose Breath Tist in Diagnosis of Diabetes Diabetes mellitus is a group of diseases characterized by high levels of blood glucose resulting from defects in insulin secretion, insulin action, or both. Diabetes can be associated with serious complications and premature death if left undiagnosed and untreated. It has been estimated by the World Health Organization that the number of people suffering from diabetes worldwide will more than double from about 135 million now to 300 million by the year 2025. Of those estimated to have diabetes, it is believed that approximately one third of those are undiagnosed. It is also known that the prevalence of diabetes increases with age. It is estimated that 0.16% of people under the age of 20 have diabetes but this number dramatically increases to 18.4% for people over the age of 65.

There are four types of diabetes; type 1 (insulin dependent) represents 5 to 10% of all diagnosed cases, type 2 (non-insulin-dependent diabetes) represents 90 to 95% of all diagnosed cases, gestational diabetes develops in 2 to 5% of all pregnancies but disappears when a pregnancy is over, and other specific types of diabetes resulting from specific genetic syndromes, surgery, drugs, malnutrition, infections and other illnesses may account for 1 to 2% of all diagnosed cases. A number of different methods exist for determining diabetes. These include postprandial blood glucose, oral glucose tolerance test (OGTT), O'Sullivan glucose tolerance test (gestational test), hemoglobin Alc, islet cell antibodies, glutamic acid decarboxylase (GAD) antibodies, and insulin antibodies. However, diabetes is most readily detected when the carbohydrate metabolic capacity is tested. This is done by stressing the system with a defined glucose load as in the OGTT.

Although the OGTT is a standard test for diabetes, it has been criticized because many of the variables affecting the test results are difficult to control for; the standardized carbohydrate diet, eight to sixteen hour fast, stress, exercise, hormone imbalances, and various drugs can cause test variables. These variables lead to poor reproducibility and limit the diagnostic usefulness of this test. In addition, the OGTT involves the collection of numerous blood specimens making it an invasive procedure.

The development of a $^{13}$C-glucose breath test for the detection of diabetes offers a non-invasive method that is not affected by the above mentioned variables. $^{13}$C is a non-radioactive isotope that occurs naturally in food and animal tissues. In the past the disadvantage of $^{13}$C had been the shortage of the gas isotope mass spectrometers used for analysis. With the ready availability of the necessary instrumentation and the $^{13}$C-labeled compounds required, the use of $^{13}$C-labeled compounds in breath tests is more feasible.
Clinical Study Objective: The primary aim of this pilot study is to evaluate the sensitivity, specificity and reliability of a $^{13}$C-D-glucose breath test in the diagnosis of type 2 and gestational diabetes as compared to the already validated glucose tolerance test that will be considered the standard.

Design: A multi-center, blinded, non-randomized design is utilized. Only the referring physicians have knowledge of the participants' status. Participants undergo a glucose tolerance test. Within two weeks following, participants undergo a $^{13}$C-D-glucose breath test. The findings from both tests are examined for concordance.

Study Participants: This investigation is carried out by recruiting 50 individuals each for type 2 and gestational diabetes. For type 2 diabetes, the participants are suspected to be diabetic. For gestational diabetes, the participants are women in their $24^{th}$ to $28^{th}$ week of pregnancy who have presented for the standard gestational diabetes mellitus screening test. Any diagnosis of diabetes is based on the results of the glucose tolerance test.

Testing Strategy: Eligible participants, after giving informed consent, undergo the glucose tolerance test and the $^{13}$C-D-glucose breath test separated by a minimum of 24 hours and a maximum of two weeks. The glucose tolerance test is performed according to the guidelines of the Canadian Diabetes Association (CMAJ, JAMC Oct. 20, 1998;159(8 suppl):S1-S29). Briefly, for the gestational diabetes screen, the glucose tolerance test consists of the consumption of a 50 g glucose tolerance drink and the collection of a venous blood sample one hour later for glucose determination. For the time between the drink consumption and the blood sampling, the participant remains sedentary and refrains from smoking or eating. Small sips of water may be taken if necessary.

For type 2 diabetes, an overnight fast (10–16 hours) precedes the glucose tolerance test. A fasting glucose blood sample is drawn prior to the consumption of a 75 g glucose tolerance drink. Two hours after the ingestion of the drink, a venous blood sample is collected for glucose determination. For the time between the drink consumption and the blood sampling, the participant remains sedentary and refrains from smoking or eating. Small sips of water may be taken if necessary.

The $^{13}$C-D-glucose breath test is preceded by an overnight fast (minimum eight hours). After fasting, the participants are required to provide a baseline breath sample. The participants then ingest the $^{13}$C-D-glucose drink preparation and will provide breath samples at 1, 1.5, and 2 hours. During the test the participants remain sedentary and are not permitted to smoke or eat. Only small sips of water are permitted during the test.

Overall Study Design: A total of 50 participants are investigated each for type 2 and gestational diabetes.

Visit One: During the recruitment process, each individual is asked to review a Participant Information Sheet and to talk with the laboratory personnel to ensure that all eligibility requirements are met. The individual is given an opportunity to ask questions and if they meet all the eligibility criteria, they are asked to read and sign and Informed Consent Form.

All participants who have met the eligibility criteria and signed a consent form are tested by both the glucose tolerance test (Visit Two) and the $^{13}$C-D-glucose breath test (Visit Three) separated by a minimum of 24 hours and a maximum of two weeks.

Visit Two: The glucose tolerance test follows the guidelines set out by the Canadian Diabetes Association (CMAJ, JAMC Oct. 20, 1998; 159(8 suppl):S1-S29). Briefly for the gestational diabetes screen, the participants are asked to consume a commercially available glucose tolerance drink consisting of 50 g of dextrose in 296 ml. One hour following consumption, a venous blood sample is collected into a red-topped vacutainer tube. For type 2 diabetes, participants first complete and overnight fast (10–16 hours) and then provide a fasting blood glucose sample. Participants then ingest a commercially available glucose tolerance drink consisting of 75 g of dextrose in 296 ml followed by the collection of a venous blood sample 2 hours post-consumption.

Visit Three: For the $^{13}$C-D-glucose breath test, participants first complete an overnight fast (minimum of 8 hours). Participants provide a baseline breath sample which is followed by consumption of a $^{13}$C-D-glucose-enriched solution containing 25 mg of $^{13}$C-D-glucose in combination with 15 g of unlabeled USP dextrose in 100 ml of water.

Participants then provide breath samples at 1, 1.5, and 2 hours.

Note: Visit One and Visit Two may be combined if it is more convenient and all the testing criteria are met.

NUMBER OF PARTICIPANTS AND TARGET POPULATION: A total of 100 adult participants (18 years of age or older) who are suspected of having type 2 diabetes (n=50) or are being screened for gestational diabetes (n=50) are recruited from those individuals presenting for the oral glucose tolerance test.

INTERIM ANALYSIS: After 25 participants are enrolled for a particular type of diabetes, all parties are unblinded to the participants' status. At this point in the study, the results are evaluated. If the $^{13}$C-D-glucose breath test results do not correlate with the standard, the oral glucose tolerance test, such that greater than 5% of the participants are reported as false negatives or false positives, the study is temporarily halted. If the study is halted, the protocol is amended to reflect an adjustment in the $^{13}$C-D-glucose breath test kit components such that it contains 50 mg of $^{13}$C-D-glucose and 15 g of unlabeled USP dextrose.

EXAMPLE 11

Advantages of the $^{13}$C Glucose Test for the Diagnosis of Diabetes

The disadvantages of the OGTT include uncontrollable factors which cause variability or spurious results and the invasiveness of the test. Other tests known in the are not specific, are invasive, are variable and are labor intensive. The $^{13}$C glucose breath test of the present invention is sensitive, reliable and specific. The $^{13}$C glucose breath test shows minimal intra-individual variation, excellent analytical precision and breath specimens are stable for at least six weeks at room temperature. The $^{13}$C glucose breath test is preferred over tests known in the art, it is non-invasive, easy to perform, has very good sensitivity and specificity and is cost effective. A preferred use of the breath test of this invention is for the diagnosis of type 2 and gestational diabetes. This invention is also preferred to determine the level of insulin resistance and for monitoring the appropriateness of the therapy of diabetes patients.

EXAMPLE 12

Efficacy of the C-glucose Breath Test in the Detection of Type 2 Diabeted and Insulin Resistance Fifty-four diabetic subjects, aged 18–75, were recruited from attendees of the University of Alberta Hospital diabetes education program. All such subjects who took part in this study did so after attending the program wherein their diabetic status was verified by an endocrinologist according to WHO diagnostic criteria (12). Patients with secondary forms of diabetes or who were on medications which might otherwise interfere with insulin sensitivity were excluded. Similarly, patients in whom a 12-hour medication-free run-in period or fast was thought to be medically contraindicated were excluded from this study. Fifty normal subjects were recruited from the population-at-large as well as from spouses of participating diabetic patients. We report results for only type 2 diabetics in this study although we have carried out the protocol in a few carefully selected type 1 diabetics for verification. This project was approved by the Research Ethics Board of the University of Alberta Faculty of Medicine and all subjects gave their informed consent prior to participating in the study.

In this study, each subject underwent breath testing as well as a standard 75 g oral glucose tolerance test (OGTT) in random order. Following a 12-hour overnight fast, study subjects attended the University of Alberta Hospital Metabolic Center at 8:00 a.m. No anti-diabetic medications, including insulin, were taken within 12 hours of the study and, in particular, glyburide was not taken within 24 hours of the study. Subjects were allowed free access to water during the fast, however. At time zero of the standard glucose tolerance test, a serum insulin level was also obtained in a proportion of study subjects. This modification to the protocol was added after a planned interim analysis indicated enhanced sensitivity of the breath test over OGTT parameters. Plasma glucose was measured by glucose oxidase methodology and serum insulin was measured by automated immunoassay (Elecsys 2010®, Roche Diagnostic, Basel, Switzerland). For the breath test, subjects provided a baseline breath sample and then drank 250 ml of the breath test solution. Serial breath samples were obtained at 1, 1.5 and 2 hours after consumption of the breath test solution. Capillary blood glucose readings were obtained every 30 minutes during the 2 hours of the breath test.

The $^{13}$C breath test consisted of 25 mg of $^{13}$C-glucose mixed with 15 g of dextrose and orange flavoring. The $^{13}$C-glucose (Martek Biosciences Corporation, Maryland, USA) is universally labeled meaning the $^{13}$C occupies all six carbon positions in the molecule. Previous optimization studies had demonstrated that 25 mg of $^{13}$C-glucose was sufficient for diagnostic purposes and that 15 g of glucose provided an adequate caloric challenge. In order to carry out the test, a baseline breath sample was obtained followed by breath samples at 1, 1.5 and 2 hours following the test drink. The expired $^{13}$CO$_2$ following test drink ingestion was compared to the baseline value and results expressed as an absolute increase in $^{13}$C in δ per mil. Although optimization studies suggested 1.5 hours as the best time for breath sampling, we included 1 and 2 hour time points to verify these findings. Similarly, although a previous receiver operated characteristics (ROC) suggested 8.5 as the cutoff between normal and abnormal, and a range of useful δs is from 8 to 10, we also repeated ROC analysis using the data in this study. On this basis a δ per mil of 9.0 was ultimately used as a cutoff between diabetic and non-diabetic for this experiment.

$^{13}$CO$_2$ was measured in breath samples using the AP2003, an isotope ratio mass spectrometer (Analytical Precision Limited, Cheshire, England). To obtain breath sample, subjects were asked to blow the value of a normal exhalation through a short straw into (10 ml) gas sampling tubes (Labco Exetainer® system—$^{13}$C and gas testing vials, Labco Limited, Buckinghamshire, England). The tubes were then immediately stoppered until analyzed. These tubes are known to be impermeable to gases for up to 90 days following sealing. Gas sampling from the tubes occurs via a needle in the AP2003 machine permeating a rubber membrane present in the cap of the tube. The same apparatus and overall method is commonly used in other $^{13}$C breath tests such as the $^{13}$C urea breath test for *Helicobacter pylori*.

A 75 gram glucose tolerance test was carried out according to standard protocol. As mentioned, a baseline fasting serum insulin level was obtained in a sub-sample of the study population. Glucose was collected in lithium-heparin tubes and immediately assayed in order to ensure no changes in apparent glucose concentration. The HOMA index was calculated as previously described using the formula HOMA=(fasting glucose×fasting insulin)/22.5(9). A value of 2.5 or above was taken to be indicative of insulin resistance.

All values are expressed as the mean ± SD unless otherwise indicated. Sensitivity, specificity, positive predictive value, negative predictive value and diagnostic accuracy were calculated according to standard methodology. Differences in variables between groups were compared using two-sided, unpaired t-tests, ANOVA or ANCOVA as appropriate. Post hoc testing for ANOVA was carried out using the Tukey test. Correlations between variables were carried out using linear regression. Logistic regression was used to determine factors which most accurately predicted diabetic status. A p value of less than 0.05 was considered statistically significant. Statistical analysis was carried out using Statview version 5.0.1 (SAS Institute, Cary, N.C., USA).

A total of 53 diabetic, 50 normal and 5 subjects with impaired glucose tolerance were included in the primary analysis. Of this total, a subgroup of 45 individuals (21 diabetic, 24 normal) underwent simultaneous measurement of fasting serum insulin along with fasting plasma glucose in order to calculate a HOMA. Mean age of diabetic patients was 54±11 and the mean age of normals was 44±14 (p<0.0001 for difference). Body mass index (BMI) of diabetics was 31.6±5.5 and that of normals 28.8±5.2 (p=0.011). Although there were differences between diabetics and normals in terms of age and BMI, using age and/or BMI as covariates did not significantly affect the results.

Figure 6A:
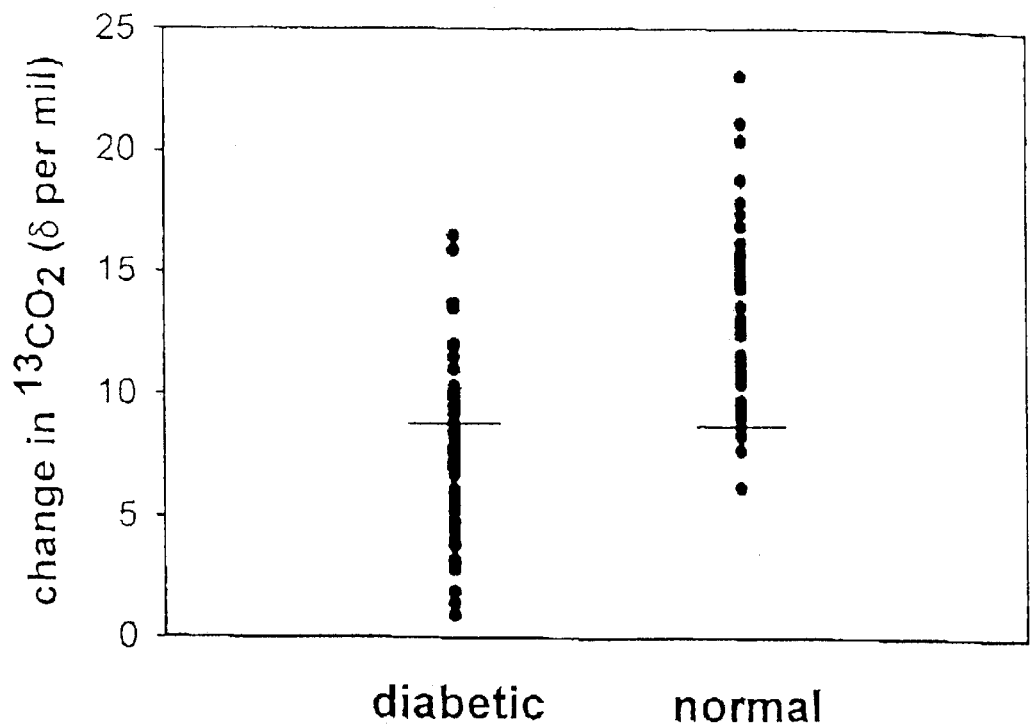
Figure 6B:
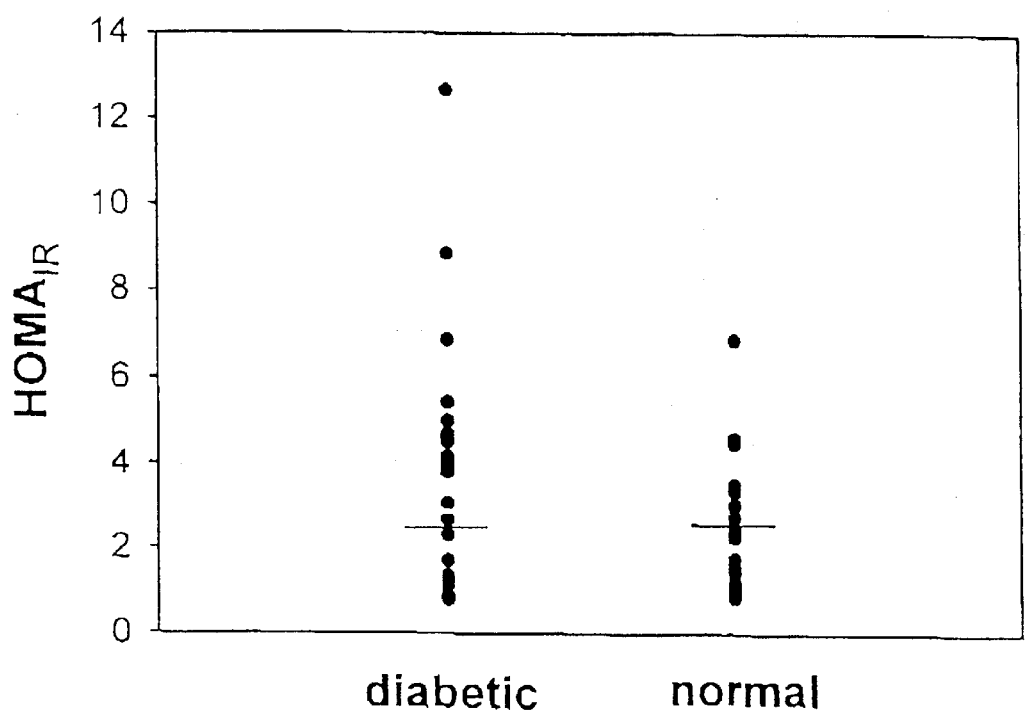

A scatter diagram for diabetics and normals for both the $^{13}$C breath test and the HOMA are shown in FIGS. 6a and 6b. From this figure, it can be seen that there is significantly less overlap between normals and diabetics for the $^{13}$C breath test results than for the HOMA index results. Table 1 compares diagnostic variables for the fasting plasma glucose, OGTT(WHO criteria), the HOMA index and the $^{13}$C breath test. As not all subjects had fasting serum insulin values measured, diagnostic parameters for the $^{13}$C breath test in the subgroup that did have their HOMA indexes calculated are presented in a separate column. For the purposes of this analysis, subject were classified as either diabetic or non-diabetic based on the criterion of a fasting plasma glucose of 7.0 or greater or a 2-hour OCTT value of 11.1 or greater. The classification of impaired fasting glucose was not used as this diagnosis is not readily verifiable from clinical data. From this table, it can be seen that the sensitivity, negative predictive value and overall diagnostic accuracy of the $^{13}$C-glucose breath test is superior to that of a fasting plasma glucose, OGTT or HOMA in the diagnosis of type 2 diabetes. Similarly, the positive predictive value and the specificity of the $^{13}$C-glucose is superior to that of the HOMA in making the diagnosis of type 2 diabetes. These latter two parameters are not applicable to the faasting plasma glucose or OGTT, however, as an abnormality in either criterion would change the status of a subject "normal" to "diabetics". Thus, based on a single measurement, there can be no false positives by fasting plasma glucose or OGTT. Indeed, one supposedly normal subject did have a fasting plasma glucose of 7.0 but for purposes of this analysis, was still considered "normal". It is noteworthy that this same individual was categorized as "diabetic" on the basis of the $^{13}$C breath test. If agreement between two fasting blood glucoses is used as a basis for diagnosis, then the estimated sensitivity of a FPG was 37%, specificity 82%, PPV 74%, NPV 48% and diagnostic accuracy 55%. However, these values are estimates, using the fasting capillary glucose as a "second FPG", taking into account an expected 15% lower glucose result for the capillary glucose compared to the FPG. Thus, the requirement for confirmation of any single diagnostic value by a repeat value would, as expected, decrease sensitivity but increase specificity.

FIG. 7 demonstrates the relationship between the 1.5-hour $^{13}$C-glucose result and the HOMA. As can be seen, a significant correlation exists between the two indices. FIG. 8 shows the ROC plot for the 1.5-hour $^{13}$C-glucose breath result. From this figure, a cutoff of 9.0 seems to provide an optimal criterion for differentiating diabetic versus non-diabetic.

Logistic regression based on clinical status as the dependent variable, and the 1.5-hour $^{13}$C breath test result, HOMA, age, BMI and sex as independent variables, gave an $R^2$ value of 0.53. Only the 1.5-hour $^{13}$C breath test result gave a significant partial correlation coefficient. When the logistic regression was repeated using either the 1.5-hour $^{13}$C breath test result or the HOMA, but not both, in addition to the other variables, only the $^{13}$C breath test result gave a significant partial correlation coefficient for the former regression. When the HOMA was used, significant partial correlations were obtained for age and HOMA. The $R^2$ for the former regression was 48 and for the latter was 0.32. Thus the $^{13}$C breath test appears to be the strongest predictor of diabetic status.

Further variations and modification of the present invention will be apparent to those skilled in the art and are intended to be encompassed by the specification and claims appended hereto.

TABLE 1

Diagnostic Parameters for the Various Tests

|  | fpg | WHO | HOMA | $^{13}$C breath | $^{13}$C breath* |
|---|---|---|---|---|---|
| sensitivity | 43 | 62 | 67 | 73 | 75 |
| specificity | (97) | (95) | 67 | 92 | 84 |
| PPV | (96) | (92) | 64 | 90 | 79 |
| NPV | 52 | 61 | 70 | 77 | 81 |
| DA | 64 | 74 | 67 | 79 | 80 | fpg = fasting plasma glucose,
$^{13}$C breath = test results from all 104 subjects,
$^{13}$C breath* = $^{13}$C breath test results from the subgroup where the HOMA was calculated,
PPV = positive predictive value,
NPV = negative predictive value,
DA = diagnostic accuracy.
Numbers in parenthesis presume normal subjects (1 for fpg and 2 for WHO) were incorrectly diagnosed as being diabetic.

What is claimed is:

1. A method of diagnosing a condition in a subject, said condition in a subject, said condition selected from the group consisting of diabetes, insulin resistance, impaired glucose tolerance, impaired fasting glucose and gestational diabetes, said method comprising:
   a) collecting a first breath sample from said subject in a first breath collection container;
   b) administering $^{13}$C-enriched glucose to said subject;
   c) collecting a second breath sample from said subject in a second breath collection container at a time point after administration of said $^{13}$C-enriched glucose;
   d) measuring $^{13}CO_2$ in each of said first and second breath samples; and
   e) comparing the amount of $^{13}CO_2$ in said second breath sample with the amount of $^{13}CO_2$ in said first breath sample to obtain a delta valve, wherein said comparison is made by choosing a delta cutoff of receiver oprated characteristics (ROC) values, wherein the sensitivity and specificity are such as to maximize diagnostic accuracy, and wherein the presence of less $^{13}CO_2$ in said second breath sample compared to normal control values indicates the presence of said condition.

2. The method of claim 1, wherein said cutoff of ROC values is 8 to 10.

3. The method of claim 2, wherein said cutoff of ROC values is 9.

4. The method of claim 1, wherein said condition is diabetes.

5. The method of claim 1, wherein said condition is insulin resistance.

6. The method of claim 1, wherein said condition is impaired glucose tolerance.

7. The method of claim 1, wherein said condition is impaired fasting glucose.

8. The method of claim 1, wherein said condition is gestational diabetes.

9. The method of claim 1, wherein said $^{13}$C-enriched glucose is uniformly labeled.

10. A method of predicting a subject's risk of developing diabetes, said method comprising:
    a) collecting a first breath sample from said subject in a first breath collection container;
    b) administering $^{13}$C-enriched glucose to said subject;
    c) collecting a second breath sample from said subject in a second breath collection container at a time point after administration of said $^{13}$C-enriched glucose;
    d) measuring $^{13}CO_2$ in each of said first and second breath samples; and
    e) comparing the amount of $^{13}CO_2$ in said second breath sample with the amount of $^{13}CO_2$ in said first breath sample, to obtain a delta value, wherein said comparison is made by choosing a delta cutoff of receiver operated characteristics (ROC) values, wherein the sensitivity and specificity are such as to maximize diagnostic accuracy, and wherein the presence of less $^{13}CO_2$ in said second breath sample compared to normal control values indicates risk of developing diabetes.

11. The method of claim 10, wherein said cutoff of ROC values is 8 to 10.

12. The method of claim 1, wherein said cutoff of ROC values is 9.

13. The method of claim 10, wherein said diabetes is type I diabetes mellitus.

14. The method of claim 10, wherein said diabetes is type II diabetes mellitus.

15. The method of claim 10, wherein said diabetes is secondary diabetes mellitus.

16. The method of claim 10, wherein said diabetes is impaired glucose tolerance.

17. The method of claim 10, wherein said diabetes is gestational glucose mellitus.

18. The method of claim 10, wherein said $^{13}$C-enriched glucose is uniformly labeled.

* * * * *

UNITED STATES PATENT AND TRADEMARK OFFICE
CERTIFICATE OF CORRECTION

PATENT NO.    : 6,461,870 B2
DATED         : October 8, 2002
INVENTOR(S)   : Yatscoff et al.

It is certified that error appears in the above-identified patent and that said Letters Patent is hereby corrected as shown below:

Title page,
Item [63], Related U.S. Application Data, replace "May 9, 1999" with
-- May 6, 1999 --.

Column 1,
Line 9, replace "May 9, 1999" with -- May 6, 1999 --

Column 5,
Line 44, replace "$^{3}$C-enriched glucose to said subject; collecting a second" with
-- $^{13}$C-enriched glucose to said subject; collecting a second --
Line 63, replace "BRIED DESCRIPTION OF THE DRAWING" with -- BRIEF DESCRIPTION OF THE DRAWING --

Column 12,
Line 16, replace "Usefulness of $^{13}$C Glucose Breath Tist in Diagnosis of"
with -- Usefulness of $^{13}$C Glucose Breath Test in Diagnosis of --

Column 16,
Line 4, replace "such as the $^{13}$C urea breath test for *Helicobacter pylon*." with
-- such as the $^{13}$C urea breath test for *Helicobacter pylori*. --
Line 47, replace "$^{13C}$ breath test. As not all subjects had fasting serum insulin"
with -- $^{13}$C breath test. As not all subjects had fasting serum insulin --
Line 63, replace "latter two parameters are not applicable to the faasting" with
-- latter two parameters are not applicable to the fasting --

Column 18,
Line 52, replace "The method of claim 1, wherein said cutoff of ROC" with -- The method of claim 11, wherein said cutoff of ROC --

Signed and Sealed this

Tenth Day of June, 2003

JAMES E. ROGAN
*Director of the United States Patent and Trademark Office*